United States Patent
von Blücher et al.

(10) Patent No.: US 7,737,083 B2
(45) Date of Patent: Jun. 15, 2010

(54) HIGH PERFORMANCE ADSORBENTS BASED ON ACTIVATED CARBON OF HIGH MICROPOROSITY

(75) Inventors: Hasso von Blücher, Erkrath (DE); Bertram Böhringer, Wuppertal (DE); Jann-Michael Giebelhausen, Rathenow (DE)

(73) Assignee: Blucher GmbH, Erkrath (DE)

( * ) Notice: Subject to any disclaimer, the term of this patent is extended or adjusted under 35 U.S.C. 154(b) by 13 days.

(21) Appl. No.: 11/974,098

(22) Filed: Oct. 11, 2007

(65) Prior Publication Data

US 2008/0107589 A1    May 8, 2008

(30) Foreign Application Priority Data

Oct. 12, 2006    (DE)    ........................ 10 2006 048 790

(51) Int. Cl.
    *C01B 31/08*    (2006.01)
(52) U.S. Cl. ........................ 502/432; 502/426; 502/437; 502/416
(58) Field of Classification Search ........................ None
    See application file for complete search history.

(56) References Cited

U.S. PATENT DOCUMENTS

| | | | | |
|---|---|---|---|---|
| 5,324,703 | A * | 6/1994 | McCue et al. | 502/424 |
| 5,576,261 | A | 11/1996 | Sudhaker et al. | 502/185 |
| 5,710,092 | A * | 1/1998 | Baker | 502/416 |
| 5,977,016 | A | 11/1999 | Von Blücher et al. | 502/426 |
| 5,993,766 | A | 11/1999 | Tom et al. | 423/294 |
| 6,184,177 | B1 | 2/2001 | Von Blücher et al. | 502/34 |
| 6,300,276 | B1 | 10/2001 | De Ruiter et al. | 502/437 |
| 7,091,156 | B2 * | 8/2006 | Hirahara et al. | 502/416 |
| 7,288,504 | B2 | 10/2007 | Von Blucher et al. | 502/432 |
| 7,538,069 | B2 * | 5/2009 | Schonfeld et al. | 502/416 |
| 2003/0092560 | A1 * | 5/2003 | Von Blucher et al. | 502/10 |

(Continued)

FOREIGN PATENT DOCUMENTS

CN    1634761 A    *    7/2005

(Continued)

OTHER PUBLICATIONS

Indo German Carbons Limited 2009.*

(Continued)

*Primary Examiner*—Melvin C Mayes
*Assistant Examiner*—Guinever S Gregorio
(74) *Attorney, Agent, or Firm*—Woodard, Emhardt, Moriarty, McNett & Henry LLP

(57) ABSTRACT

The invention concerns high performance adsorbents based on activated carbon of high microporosity which are present in the form of discrete grains of activated carbon, preferably in spherical form, and which are characterized by the following parameters:

- a Gurvich total pore volume of at least 0.7 cm$^3$/g, at least 70% of this total pore volume being formed by micropores having pore diameters of $\leq$20 Å,
- a measure of central tendency pore diameter of not more than 30 Å, and
- a BET surface area of at least 1500 m$^2$/g.

These high performance adsorbents are particularly useful for the adsorption of toxins, noxiants and odors, in particular from gas or to be more precise air streams, for purifying or cleaning gases, such as in particular air, for application in medicine or to be more precise pharmacy and as sorptive storage media for gases, in particular hydrogen.

14 Claims, 2 Drawing Sheets

U.S. PATENT DOCUMENTS

| | | |
|---|---|---|
| 2004/0038802 A1 | 2/2004 | Von Blucher et al. ......... 502/10 |
| 2008/0171648 A1 | 7/2008 | Von Blucher et al. .......... 502/9 |

FOREIGN PATENT DOCUMENTS

| | | |
|---|---|---|
| DE | 43 04 026 A1 | 2/1993 |
| DE | 43 28 219 A1 | 2/1995 |
| DE | 196 00 237 A1 | 7/1996 |
| DE | 196 25 069 A1 | 1/1998 |
| DE | 199 30 732 A1 | 1/2001 |
| JP | 2001269570 A | 10/2001 |
| JP | 2005132696 A | 5/2005 |
| WO | WO 98/07655 | 8/1997 |
| WO | WO 01/83368 A1 | 11/2001 |
| WO | WO 02/32569 A1 | 4/2002 |

OTHER PUBLICATIONS

European Council of Chemical Manufacturers' Federations, Test Methods for Activated Carbons, Item 1.6 "Mechanical Hardness", pp. 18/19, Nov. 1986.

Lowell, S., et al., Characterization of Porous Solids and Powders: Surface Area, Pore Size and Density, Particle Technology Series, vol. 16, pp. 111-112, 1st ed., Kluwer Academic Publishers, 2004.

Winnacker-Kuchler (3rd edition), vol. 7, pp. 93 seq.

Z. Anal. Chem. 238, pp. 187-193 (1968).

\* cited by examiner

HIGH PERFORMANCE ADSORBENTS BASED ON ACTIVATED CARBON OF HIGH MICROPOROSITY

CROSS REFERENCES TO RELATED APPLICATIONS

This application claims priority to German Patent Application No. DE 10 2006 048 790.7, filed Oct. 12, 2006, entitled "HIGH PERFORMANCE ADSORBENTS BASED ON ACTIVATED CARBON OF HIGH MICROPOROSITY", which is expressly incorporated by reference herein, in its entirety.

BACKGROUND OF THE INVENTION

The present invention concerns the adsorption arts. More particularly, the present invention concerns high performance adsorbents based on activated carbon of high microporosity and also its use, in particular for adsorptive filtering materials, for the adsorption of toxins, noxiants and odors, in particular from gas or to be more precise air streams, for purifying or cleaning gases, such as in particular air, for application in medicine or to be more precise pharmacy, as sorptive storage media for gases, in particular hydrogen, and the like.

Activated carbon has fairly unspecific adsorptive properties and therefore is the most widely used adsorbent. Legislative strictures as well as the rising sense of responsibility for the environment lead to a rising demand for activated carbon.

Activated carbon is generally obtained by carbonization (also referred to by the synonyms of smoldering, pyrolysis, burn-out, etc) and subsequent activation of carbonaceous compounds, preferably such compounds as lead to economically reasonable yields. This is because the weight losses through detachment of volatile constituents in the course of carbonization and through the burn-out in the course of activation are appreciable. For further details concerning the production of activated carbon, see for example H.v. Kienle and E. Bäder, Aktivkohle und ihre industrielle Anwendung, Enke Verlag Stuttgart, 1980.

The constitution of the activated carbon produced—finely or coarsely porous, firm or brittle, etc—depends on the starting material. Customary starting materials are coconut shells, wood wastes, peat, bituminous coal, pitches, but also particular plastics which play a certain part in the production of woven activated carbon fabrics for example.

Activated carbon is used in various forms: pulverized carbon, splint coal carbon, granulocarbon, molded carbon and also, since the end of the 1970s, spherical activated carbon ("spherocarbon"). Spherical activated carbon has a number of advantages over other forms of activated carbon such as pulverized carbon, splint coal carbon, granulocarbon and the like that make it useful or even indispensable for certain applications: it is free flowing, abrasion resistant or to be more precise dustless, and hard. Spherocarbon is in great demand for particular applications, for example, because of its specific form, but also because of its high abrasion resistance.

Spherocarbon is mostly still being produced today by multistage and very costly and inconvenient processes. The best known process consists in producing spherules from bituminous coal tar pitch and suitable asphaltic residues from the petrochemical industry, which are oxidized to render them unmeltable and then smoldered and activated. For example, spherocarbon can also be produced in a multistage process proceeding from bitumen. These multistage processes are very cost intensive and the associated high cost of this spherocarbon prevents many applications wherein spherocarbon ought to be preferable by virtue of its properties.

WO 98/07655 A1 describes a process for producing activated carbon spherules wherein a mixture comprising a diisocyanate production distillation residue, a carbonaceous processing aid and if appropriate one or more further additives is processed into free-flowing spherules and subsequently the spherules obtained in this way are carbonized and then activated.

It is further prior art to produce spherocarbon by smoldering and subsequent activation of new or used ion exchangers comprising sulfonic acid groups, or by smoldering ion exchanger precursors in the presence of sulfuric acid and subsequent activation, the sulfonic acid groups and the sulfuric acid respectively having the function of a crosslinker. Such processes are described for example in DE 43 28 219 A1 and DE 43 04 026 A1 and also in DE 196 00 237 A1 including the German patent-of-addition application DE 196 25 069 A1.

However, there are a number of specific applications where it is not only the geometry or to be more precise the external shape of the activated carbon which is of decisive importance, but also its porosity, in particular the total pore volume and the adsorption capacity on the one hand and the distribution of the pores, i.e., the fraction of micro-, meso- and macropores in relation to the total pore volume, on the other.

There are a number of applications requiring a particularly high microporosity of the activated carbon, i.e., a high micropore volume fraction, coupled with an altogether high total pore volume, for example in relation to the applications mentioned at the beginning, for example for the adsorption of toxins, noxiants and odors, in particular from gas or to be more precise air streams, for purifying or cleaning gases, such as in particular air, for application in medicine or to be more precise pharmacy, in the sorptive storage of gases, in particular hydrogen, in the manufacture of adsorptive filtering materials (for example for NBC protective apparel) and the like.

True, the activated carbon known for this purpose from the prior art does have a certain microporosity, but that level of microporosity is not always sufficient. In addition, increasing porosity is often observed to be accompanied by an unwelcome, occasionally unacceptable decrease in mechanical stability or to be more precise abrasion resistance. Nor are the fraction of the total pore volume which is accounted for by micropores and the absolute micropore volume always sufficient to ensure adequate performance capability for all applications.

It is an object of the present invention to provide, on the basis of activated carbon, a high performance adsorbent which is suitable for the aforementioned fields of application in particular and which at least substantially avoids or else at least ameliorates the above-described disadvantages of the prior art. More particularly, the adsorbent to be provided according to the present invention should have a high microporosity, i.e., a high microporous fraction in relation to the total pore volume and also a high micropore volume, yet at the same time also a good mechanical stability, in particular a high stability to abrasion and bursting.

By way of a solution to the problem described above, the present invention proposes—according to a first aspect of the present invention—high performance adsorbents based on activated carbon in the form of discrete grains of activated carbon, preferably in spherical form, according to claim 1. Further, in particular advantageous embodiments of the high performance adsorbents of the present invention form subject matter of the corresponding subclaims.

The present invention further provides—according to a second aspect of the present invention—the present invention's use of the high performance adsorbents according to the present invention as it is more particularly defined in the corresponding use claims.

BRIEF SUMMARY

Disclosed are high performance adsorbents based on activated carbon of high microporosity which are present in the form of discrete grains of activated carbon, preferably in spherical form, and which are characterized by the following parameters:

- a Gurvich total pore volume of at least 0.7 cm$^3$/g, at least 70% of this total pore volume being formed by micropores having pore diameters of $\leq 20$ Å,
- a measure of central tendency pore diameter of not more than 30 Å, and
- a BET surface area of at least 1500 m$^2$/g.

These high performance adsorbents are particularly useful for the adsorption of toxins, noxiants and odors, in particular from gas or to be more precise air streams, for purifying or cleaning gases, such as in particular air, for application in medicine or to be more precise pharmacy and as sorptive storage media for gases, in particular hydrogen.

DETAILED DESCRIPTION

Figure 1:
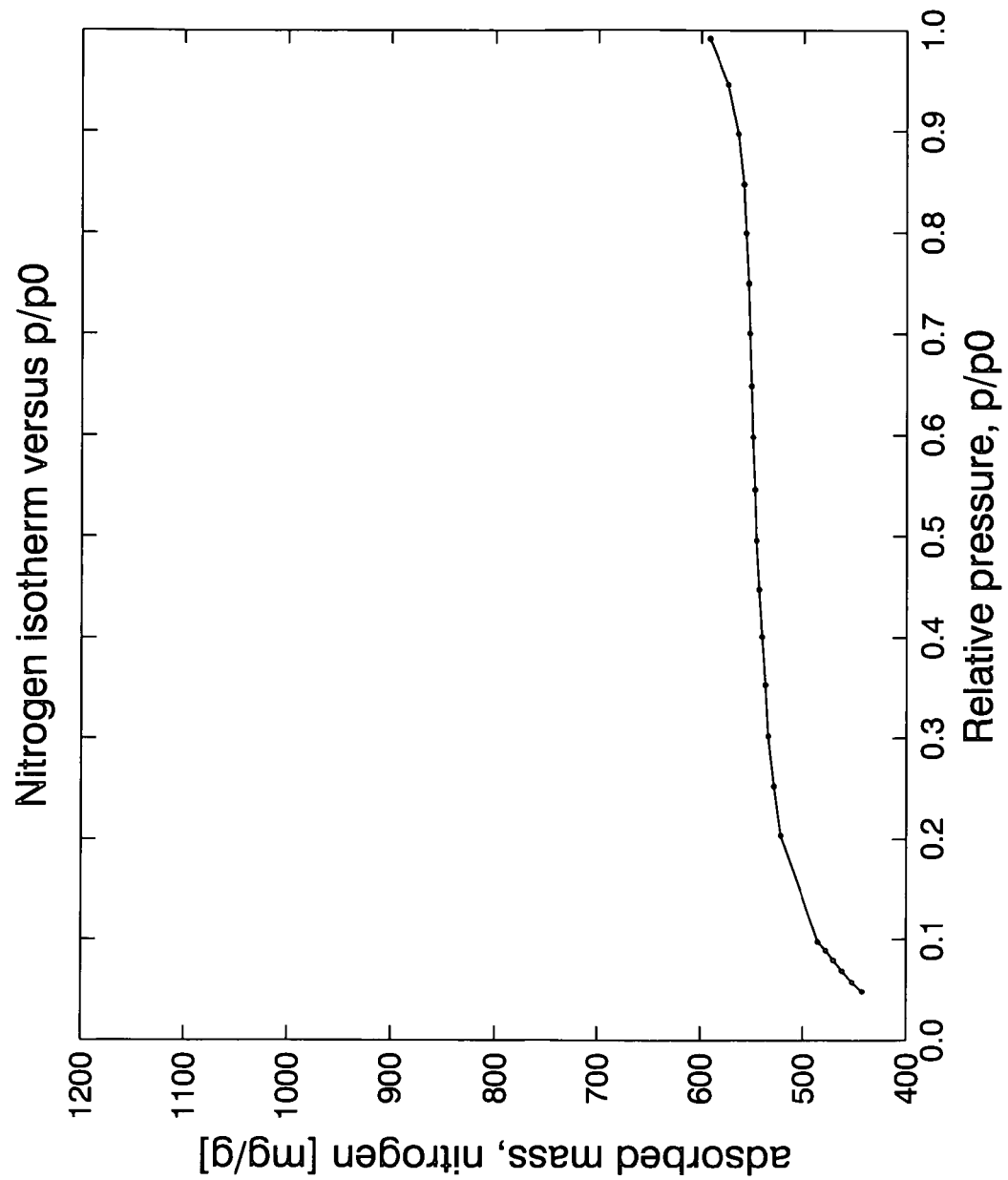
FIG. 1 is a graph showing N$_2$ adsorption isotherms for two different high performance adsorbents of the present invention.

For the purposes of promoting an understanding of the disclosure, reference will now be made to the embodiments illustrated in the drawings and specific language will be used to describe the same. It will nevertheless be understood that no limitation of the scope of the disclosure is thereby intended, such alterations and further modifications in the illustrated device and its use, and such further applications of the principles of the disclosure as illustrated therein being contemplated as would normally occur to one skilled in the art to which the disclosure relates.

The present invention accordingly provides—according to a first aspect of the present invention—high performance adsorbents based on activated carbon in the form of discrete grains of activated carbon, preferably in spherical form, characterized by the following parameters:

- a Gurvich total pore volume of at least 0.7 cm$^3$/g, at least 70% of this total pore volume being formed by micropores having pore diameters of $\leq 20$ Å,
- a measure of central tendency pore diameter of not more than 30 Å, and
- a BET surface area of at least 1500 m$^2$/g.

The present invention's high performance adsorbents or to be more precise activated carbons are notable in particular for a large total porosity and a simultaneously large BET surface area. As will be shown in what follows, the mechanical strength, in particular the abrasion resistance and the bursting or to be more precise compressive strength, of the present invention's high performance adsorbents is despite the high porosity extremely high—in contrast to comparable high-porosity activated carbons of the prior art—so that the present invention's high performance adsorbents or to be more precise activated carbons are also suitable for applications where they are exposed to large mechanical loads.

In relation to all the parameter indications hereinabove and hereinbelow, it is to be noted that the recited limits, in particular upper and lower limits, are included, i.e., all statements of values are to be understood as including the respective limits. It will further be understood that in an individual case or in relation to an application it may be necessary if appropriate to depart slightly from the limits mentioned without leaving the realm of the present invention.

The hereinabove and hereinbelow mentioned parameter data are determined using standardized or explicitly indicated methods of determination or using methods of determination familiar per se to one skilled in the art. The parameter data concerning the characterization of the porosity each follow from the nitrogen isotherm of the measured activated carbon.

The Gurvich determination of total pore volume is a method of measurement/determination known per se in this field to a person skilled in the art. For further details concerning the Gurvich determination of total pore volume reference may be made for example to L. Gurvich (1915), J. Phys. Chem. Soc. Russ. 47, 805, and also to S. Lowell et al., Characterization of Porous Solids and Powders: Surface Area Pore Size and Density, Kluwer Academic Publishers, Article Technology Series, pages 111 et seq.

The BET method of determining the specific surface area is in principle known as such to one skilled in the art, so that no further details need be furnished in this regard. All BET surface area data are based on the ASTM D6556-04 method of determination. The present invention utilizes the Multi-Point BET (MP-BET) method of determination in a partial pressure range p/p$_0$ of 0.05 to 0.1.

With regard to further details concerning the determination of the BET surface area or to be precise concerning the BET method, reference may be made to the aforementioned ASTM D6556-04 standard and also to Römpp Chemielexikon, 10th edition, Georg Thieme Verlag, Stuttgart/New York, headword: "BET-Methode", including the references cited therein, and to Winnacker-Küchler (3rd edition), Volume 7, pages 93 ff, and also to Z. Anal. Chem. 238, pages 187 to 193 (1968).

The determination of the measure of central tendency pore diameter is done on the basis of the respective nitrogen isotherms.

The Gurvich total pore volume of the high performance adsorbents of the present invention is at least 0.7 cm$^3$/g, in particular at least 0.8 cm$^3$/g, preferably at least 0.9 cm$^3$/g and more preferably at least 1.0 cm$^3$/g, and can reach values up to 1.5 cm$^3$/g, in particular up to 1.6 cm$^3$/g and preferably up to 1.8 cm$^3$/g.

In general, the Gurvich total pore volume of the high performance adsorbents of the present invention is in the range from 0.7 to 1.8 cm$^3$/g, in particular in the range from 0.8 to 1.6 cm$^3$/g and preferably in the range from 0.9 to 1.5 cm$^3$/g.

It is one particular feature of the high performance adsorbents of the present invention that they have a very large Gurvich total pore volume, so that a large adsorptive capacity is provided, with a high proportion accounted for by micropores.

In general, at least 70%, in particular at least 75%, preferably at least 80%, more preferably at least 85% and most preferably at least 90% of the Gurvich total pore volume of the high performance adsorbents of the present invention is formed by micropores having pore diameters of $\leq 20$ Å.

In general, 70% to 95%, in particular 75% to 90% and preferably 75% to 85% of the Gurvich total pore volume of the high performance adsorbents of the present invention is formed by micropores having pore diameters of ≦20 Å.

For the purposes of the present invention, micropores are pores having pore diameters up to 20 Å inclusive, mesopores are pores having pore diameters of >20 Å to 50 Å inclusive, and macropores are pores having pore diameters >50 Å.

Owing to their high microporosity, the micropore volume of the high performance adsorbents of the present invention is relatively high in that in general the carbon black method micropore volume of the high performance adsorbents of the present invention which is formed by micropores having pore diameters of ≦20 Å is in the range from 0.5 to 1.4 cm$^3$/g, in particular in the range from 0.6 to 1.2 cm$^3$/g and preferably in the range from 0.7 to 1.1 cm$^3$/g.

The carbon black method of determination is known per se to one skilled in the art, so that no further details are needed in this regard. In addition, for further details of the carbon black method of determining the pore surface area and the pore volume reference is made for example to R. W. Magee, Evaluation of the External Surface Area of Carbon Black by Nitrogen Adsorption, Presented at the Meeting of the Rubber Division of the American Chem. Soc., Oct. 1994, for example cited in: Quantachrome Instruments, AUTOSORB-1, ASI WinVersion 1.50, Operating Manual, OM, 05061, Quantachrome Instruments 2004, Fla., USA, pages 71 ff.

Owing to the high microporosity of the high performance adsorbents of the present invention, the measure of central tendency pore diameter is relatively low in that in general it is not more than 30 Å, in particular not more than 26 Å, preferably not more than 25 Å and most preferably not more than 24 Å. In general, the measure of central tendency pore diameter of the high performance adsorbents of the present invention is in the range from 15 to 30 Å, in particular in the range from 16 to 26 Å, preferably in the range from 17 to 25 Å and more preferably in the range from 18 to 24 Å.

As stated, one particular feature of the high performance adsorbents of the present invention is the relatively large BET surface area, which is at least 1500 m$^2$/g, preferably at least 1525 m$^2$/g, more preferably at least 1550 m$^2$/g and most preferably at least 1575 m$^2$/g.

In general, the BET surface area of the high performance adsorbents of the present invention is in the range from 1500 m$^2$/g to 2750 m$^2$/g, in particular in the range from 1525 to 2500 m$^2$/g, preferably in the range from 1550 to 2400 m$^2$/g and more preferably in the range from 1575 to 2350 m$^2$/g.

Similarly, the weight- and volume-based volume $V_{ads}(N_2)$ of the high performance adsorbents of the present invention at different partial pressures p/p$_0$ is very large:

The weight-based adsorbed N$_2$ volume $V_{ads(wt)}$ of the high performance adsorbents of the present invention, determined at a partial pressure p/p$_0$ of 0.25, is at least 400 cm$^3$/g and in particular at least 420 cm$^3$/g and in particular in the range from 400 to 800 cm$^3$/g, preferably in the range from 410 to 750 cm$^3$/g and more preferably in the range from 420 to 700 cm$^3$/g.

In general, the volume-based adsorbed N$_2$ volume $V_{ads(vol)}$ of the high performance adsorbents of the present invention, determined at a partial pressure p/p$_0$ of 0.25, is at least 200 cm$^3$/cm$^3$ and in particular at least 220 cm$^3$/cm$^3$ and in particular in the range from 200 to 300 cm$^3$/cm$^3$, preferably in the range from 210 to 275 cm$^3$/cm$^3$ and more preferably in the range from 225 to 260 cm$^3$/cm$^3$.

In general, the weight-based adsorbed N$_2$ volume $V_{ads(wt)}$ of the high performance adsorbents of the present invention, determined at a partial pressure p/p$_0$ of 0.995, is at least 450 cm$^3$/g and in particular at least 460 cm$^3$/g and in particular in the range from 450 to 900 cm$^3$/g, preferably in the range from 460 to 875 cm$^3$/g and more preferably in the range from 470 to 850 cm$^3$/g.

In general, the volume-based adsorbed N$_2$ volume $V_{ads(vol)}$ of the high performance adsorbents of the present invention, determined at a partial pressure p/p$_0$ of 0.995, is at least 250 cm$^3$/cm$^3$ and in particular at least 260 cm$^3$/cm$^3$ and in particular in the range from 250 to 400 cm$^3$/cm$^3$, preferably in the range from 260 to 350 cm$^3$/cm$^3$ and more preferably in the range from 265 to 320 cm$^3$/cm$^3$.

A further particular feature of the high performance adsorbents of the present invention is the large micropore surface area, i.e., the large surface area formed by pores having pore diameters of ≦20 Å. In general, the carbon black method micropore surface area of the high performance adsorbents of the present invention which is formed from pores having pore diameters of ≦20 Å is at least 1400 m$^2$/g, in particular at least 1450 m$^2$/g and preferably at least 1500 m$^2$/g, and is generally in the range from 1400 to 2500 m$^2$/g, in particular in the range from 1450 to 2400 m$^2$/g and preferably in the range from 1500 to 2300 m$^2$/g.

In addition, the high performance adsorbents of the present invention have an extremely high butane adsorption and simultaneously an extremely high iodine number, which fact characterizes their property of having excellent adsorption properties with regard to a wide variety of materials to be adsorbed.

The ASTM D5742-95/00 butane adsorption of the high performance adsorbents of the present invention is generally at least 25%, in particular at least 30% and preferably at least 40%. In general, the high performance adsorbents of the present invention have an ASTM D5742-95/00 butane adsorption in the range from 25% to 80%, in particular in the range from 30 to 70% and preferably in the range from 35 to 65%.

The ASTM D4607-94/99 iodine number of the high performance adsorbents of the present invention is generally at least 1350 mg/g, in particular at least 1450 mg/g and preferably at least 1500 mg/g. The high performance adsorbents of the present invention preferably have an ASTM D4607-94/99 iodine number in the range from 1350 to 2100 mg/g, in particular in the range from 1450 to 2050 mg/g and preferably in the range from 1500 to 2000 mg/g.

Despite their high porosity in particular microporosity, the high performance adsorbents of the present invention have a high compressive or bursting strength (resistance to weight loading) and also an extremely high abrasion resistance.

The compressive or bursting strength (resistance to weight loading) per activated carbon grain, in particular per activated carbon spherule, is at least 10 newtons, in particular at least 15 newtons and preferably at least 20 newtons. In general, the compressive or bursting strength (resistance to weight loading) per activated carbon grain, in particular per activated carbon spherule, ranges from 10 to 50 newtons, in particular from 12 to 45 newtons and preferably from 15 to 40 newtons.

As mentioned, the abrasion hardness of the high performance adsorbents of the present invention is also extremely high in that the abrasion resistance when measured by the method of CEFIC (Conseil Européen des Féderations des l'Industrie Chimique, Avenue Louise 250, Bte 71, B-1050 Brussels, Nov. 1986, European Council of Chemical Manufacturers' Federations, Test Methods for Activated Carbons, Item 1.6 "Mechanical Hardness", pages 18/19) is always 100%. Similarly, when measured according to ASTM D3802 the abrasion resistance of the high performance adsorbents of the present invention always scores 100%.

Therefore, the assignee company has developed a modified test method on the lines of this CEFIC method in order that more meaningful values may be obtained. The modified method of determination provides a better simulation of the resistance of the sample or to be more precise of the high performance adsorbents to abrasion or attrition under near actual service conditions. For this purpose, the sample is exposed to standardized conditions for a defined time in a horizontally swinging grinding cup charged with a tungsten carbide ball. The procedure adopted for this purpose is as follows: 200 g of a sample are dried for one hour at (120±2)° C. in a circulating air drying cabinet (type: Heraeus UT 6060 from Kendro GmbH, Hanau) and are subsequently cooled down in a dessicator over drying agent to room temperature. 50 g of the dried sample are removed and sieved off by means of a sieving machine equipped with an analytical sieve (type: AS 200 control from Retsch GmbH, Hanau) at a swing amplitude of 1.2 mm for ten minutes through an analytical sieve (analytical sieve of mesh size: 0.315 mm, diameter: 200 mm, height: 15 mm); the subsize grain is discarded. 5 ml of the nominal grain are filled into a 10 ml graduated cylinder to DIN ISO 384 (volume: 10 ml, height: 90 mm) and the weight is accurately determined to 0.1 mg using an analytical balance (type: BP121S from Sartorius A G, Göttingen, weighing range: 120 g, accuracy class: E2, readability: 0.1 mg) by means of a weighing glass having a ground glass lid (volume: 15 ml, diameter: 35 mm, height: 30 mm). The weighed sample is placed together with a tungsten carbide grinding ball of 20 mm diameter in a 25 ml grinding cup with screw action closure (volume: 25 ml, diameter: 30 mm, length: 65 mm, material of construction: stainless steel) and then the abrasion test is carried out by means of a swing mill (type: MM301 from Retsch GmbH, Haan, swing mill with grinding cup); the grinding cup swings in a horizontal position for one minute at a frequency of 10 Hz in the swing mill, causing the grinding ball to impact on the sample and thus create abrasion. Subsequently, the sample is sieved off by means of a sieving machine at a swing amplitude of 1.2 mm for five minutes through the aforementioned analytical sieve, the subsize grain again being discarded and the nominal grain greater than 0.315 mm being weighed back accurately to 0.1 mg in the weighing glass with lid. The abrasion hardness is computed as a mass fraction in % by the following formula: abrasion hardness [%]=(100× back-weighed weight [g])/original weight [g].

According to this method of determination, modified by the assignee company by modifying the aforementioned CEFIC standard, the abrasion resistance of the high performance adsorbents of the present invention is at least 95%, in particular at least 96%, preferably at least 97%, more preferably at least 98% and most preferably at least 99%.

The high performance adsorbents of the present invention are based on granular, in particular spherical, activated carbon whose measure of central tendency particle diameter, determined to ASTM D2862-97/04, ranges from 0.01 to 1.0 mm, in particular from 0.1 to 0.8 mm, preferably from 0.2 to 0.7 mm and more preferably from 0.4 to 0.55 mm.

The ash content of the high performance adsorbents of the present invention, determined to ASTM D2866-94/04, is not more than 1%, in particular not more than 0.8%, preferably not more than 0.6% and more preferably not more than 0.5%.

The ASTM D2867-04/04 moisture content of the high performance adsorbents of the present invention is not more than 1%, in particular not more than 0.5%, preferably not more than 0.2%.

The high performance adsorbents of the present invention generally have a bulk density, determined to ASTM B527-93/00, in the range from 250 to 750 g/l, in particular in the range from 300 to 700 g/l, preferably in the range from 300 to 650 g/l and more preferably in the range from 350 to 600 g/l.

The carbon black method external pore volume of the high performance adsorbents of the present invention is generally in the range from 0.05 to 0.5 $cm^3/g$ and in particular in the range from 0.1 to 0.45 $cm^3/g$. In general the carbon black method external pore volume of the high performance adsorbents of the present invention forms not more than 35% and preferably not more than 30% of the total pore volume and in particular 10% to 35% and preferably 14 to 30% of the total pore volume.

The carbon black method external pore surface area of the high performance adsorbents of the present invention is generally in the range from 50 to 300 $m^2/g$, in particular in the range from 60 to 250 $m^2/g$ and preferably in the range from 70 to 200 $m^2/g$. In general the carbon black method external pore surface area of the high performance adsorbents of the present invention forms not more than 15%, preferably not more than 10% of the total pore surface area and in particular 4 to 15%, preferably 4 to 12% of the total pore surface area.

The high performance adsorbents of the present invention are obtainable by carbonization and subsequent activation of gel-form sulfonated styrene-divinylbenzene copolymers, in particular sulfonated divinylbenzene-crosslinked polystyrenes, in grain form, preferably in spherical form. The divinylbenzene content of the sulfonated styrene-divinylbenzene copolymers used as starting materials to produce the high performance adsorbents of the present invention should in particular be in the range from 1% to 15% by weight and preferably in the range from 2% to 10% by weight, based on the styrene-divinylbenzene copolymers. The starting copolymers have to be selected from the gel type in order that a microporous structure may form.

When unsulfonated starting materials are used, the sulfonation can be carried out in situ, in particular using methods known per se to one skilled in the art, preferably by means of sulfuric acid and/or oleum. This is familiar per se to one skilled in the art.

Starting materials which will prove particularly advantageous are the gel-form types of the corresponding ion exchange resins or of the corresponding precursors of ion exchange resins which still have to be sulfonated.

The carbonization (also known by the synonyms of pyrolysis, burn-out or smoldering) converts the carbonaceous starting polymers to carbon; that is, in other words, the carbonaceous starting material is carboned, or carbonized. Carbonization of the aforementioned, gel-form organic polymeric grains, in particular polymeric spherules, based on styrene and divinylbenzene which comprise sulfonic acid groups leads to the detachment of the sulfonic acid groups during the carbonization and hence to free radicals and thus to crosslinks without which there would be no pyrolysis residue (=carbon). In general, the carbonization is carried out under an inert atmosphere (for example nitrogen) or an at most slightly oxidizing atmosphere. It can similarly be advantageous for the inert atmosphere of the carbonization, in particular if it is carried out at comparatively high temperatures (for example in the range from about 500° C. to 650° C.) to be admixed with a minor amount of oxygen, in particular in the form of air (for example 1 to 5%) in order that an oxidation of the carbonized polymeric skeleton may be effected and the subsequent activation may thereby be facilitated. In general, the carbonization is carried out at temperatures of 100 to 950° C., in particular 150 to 900° C. and preferably 300 to 850° C. The total time for the carbonization is approximately in the range from 30 minutes to 6 hours.

Following the carbonization, the carbonized intermediate product is subjected to an activation resulting, at the end of which, in the present invention's high performance adsorbents based on activated carbon in grain form, in particular spherical form. The basic principle of the activation is to degrade a portion of the carbon generated during the carbonization, selectively and specifically under suitable conditions. This gives rise to numerous pores, fissures and cracks, and the surface area per unit mass increases appreciably. Activation thus involves a specific burn-out of the carbon. Since carbon is degraded in the course of activation, this operation goes hand in hand with a loss of substance which—under optimal conditions—is equivalent to an increase in the porosity and in the internal surface area and in the pore volume. Activation is therefore carried out under selective or to be more precise policed oxidizing conditions. Activation is generally carried out at temperatures of 700 to 1300° C., in particular 800 to 1200° C., and preferably 900 to 1100° C.

The special feature of how the high performance adsorbents of the present invention are produced, as well as the selection of the starting material described above, resides in the specific management of the activation process, in particular in the length of the activation process combined with the activation atmosphere selected. The inventors have surprisingly determined that operating the activation process for an extremely long time, in particular 12 to 30 hours, preferably 19 to 23 hours, under a merely weakly oxidizing atmosphere, comprising but small amounts of water vapor in an otherwise nitrogen-containing atmosphere, specifically amounts of only about 0.1% to 5% by volume and in particular 0.5% to 4% by volume of water vapor, and proceeding from the selected starting materials results in the present invention's high performance adsorbents of high microporosity and high mechanical stability with the other properties described above.

Surprising is in particular that, first, the extremely long activation time does not lead to a harmful, excessive burn-out under appreciable loss of substance and, secondly, that an extremely high abrasion resistance and mechanical compressive strength result despite the high porosity coupled with high microporosity. It was unforeseeable that such long activation times do not lead to a disadvantageous result and that such long activation times cause predominantly the microporosity or the micropore volume to be generated selectively, provided the process proceeds from the gel-form starting materials as defined above.

The microporosity can then be adjusted to specific values by varying the activation times, in particular in the range from 12 to 30 hours and preferably in the range from 19 to 23 hours. The high performance adsorbents of the present invention can thus be custom tailored so to speak.

Figure 2:
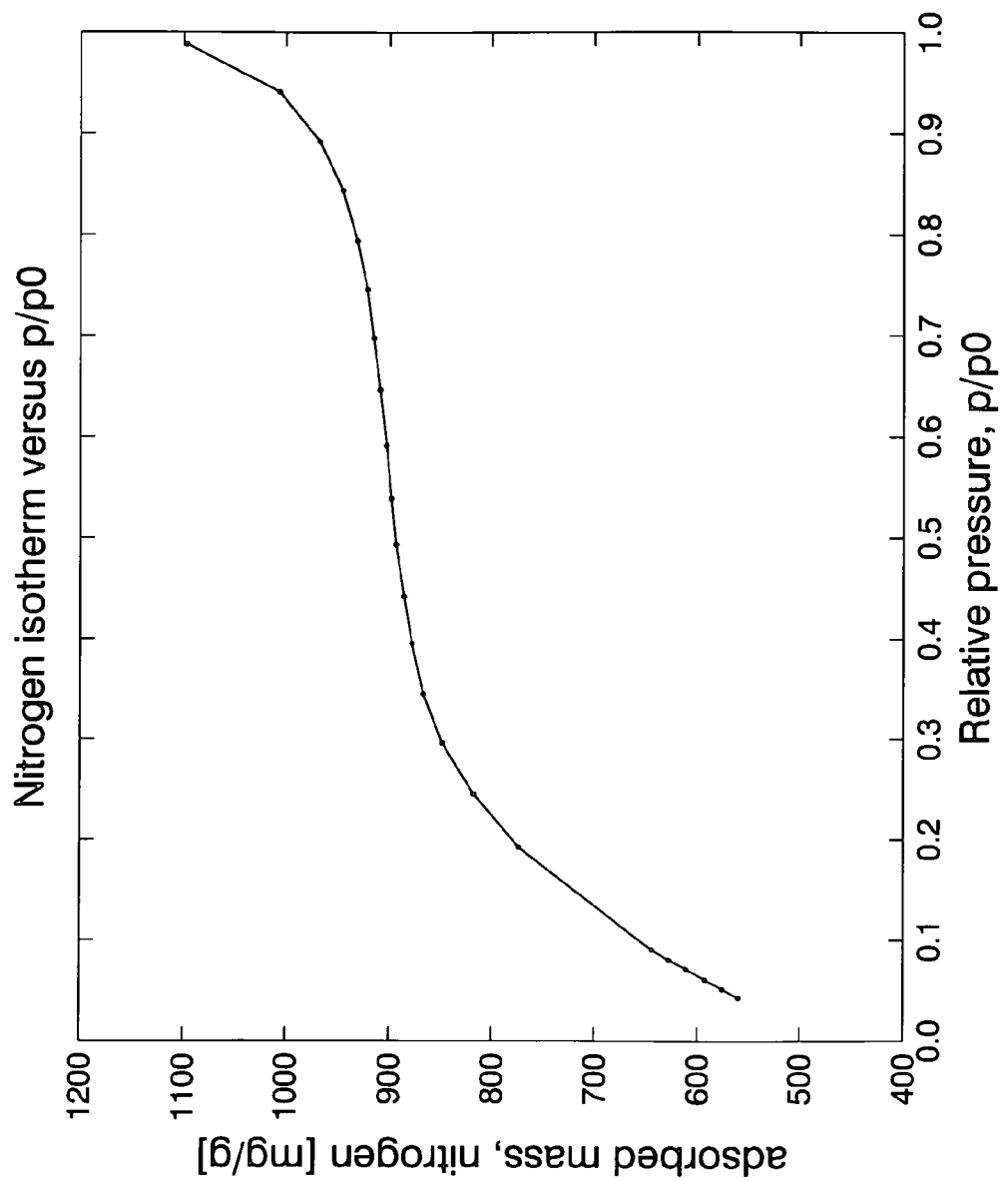
FIG. 2 is a graph showing N$_2$ adsorption isotherms for two different high performance adsorbents of the present invention.

The graphs in FIGS. 1 and 2 show $N_2$ adsorption isotherms for two different high performance adsorbents of the present invention, which were produced using activation times of differing length. The physical-chemical properties of the two high performance adsorbents of the present invention are also summarized in table 1 below. For comparison, a commercially available microporous activated carbon from Kureha is also listed therein with the physical-chemical properties in question.

The data reported in table 1 show the superiority of the high performance adsorbents of the present invention over a microporous activated carbon of the prior art in that the combination of a high total porosity with a high micropore volume fraction at high BET surface area and also high mechanical durability (compressive or bursting strength and also abrasion resistance) and excellent adsorption properties (high butane adsorption and iodine number) is in this combination—as well as the other physical-chemical parameters—only to be found in the high performance adsorbents of the present invention. The present invention thus makes it possible to produce highly microporous high performance adsorbents based on activated carbon in grain form, in particular spherical form, which are superior to commercially available products.

The inventive high performance adsorbents "activated carbon I" and "activated carbon II" recited in table 1 are each produced as follows: commercially available ion exchanger precursors of the gel type based on divinylbenzene-crosslinked polystyrene copolymers having a divinylbenzene content of about 4% are initially predried to remove the approximately 50% water fraction and subsequently sulfonated in a conventional manner at temperatures of 100° C. to 150° C. using a sulfuric acid/oleum mixture. This is followed in a conventional manner by carbonization at temperatures up to 950° C. for four hours under nitrogen and subsequently the inception of activation by adding small amounts of water vapor (about 1% to 3% by volume), to the nitrogen atmosphere; the addition of water vapor is maintained to regulate the water vapor fraction in this way. The activation process is operated for 19 hours ("activated carbon I") and 23 hours ("activated carbon II"). After cooling down to room temperature, the inventive products recited in table 1 are obtained.

The present invention further provides—according to a second aspect of the present invention—the present invention's use of the high performance adsorbents according to the present invention.

The high performance adsorbents of the present invention are particularly useful for the adsorption of toxins, noxiants and odors, for example from gas or to be more precise air streams. The high performance adsorbents of the present invention are further useful for purifying and cleaning gases, in particular for purifying air.

The high performance adsorbents of the present invention can further be used in adsorptive filtering materials or in the manufacture of adsorptive filtering materials. Such adsorptive filtering materials are useful in particular in the manufacture of protective apparel, for example protective suits, protective gloves, protective underwear, protective footwear, etc., in particular for the civilian or military sector (for example NBC protection).

The high performance adsorbents of the present invention are further useful in the sector of medicine or pharmacy, in particular as a medicament or medicament constituent.

The high performance adsorbents of the present invention can finally also be used as sorptive storage media for gases, in particular hydrogen.

Owing to their high total porosity coupled with high microporosity and also excellent mechanical stability with excellent adsorptive properties, the high performance adsorbents of the present invention are distinctly superior to prior art adsorbents of comparable microporosity.

Further embodiments, modifications and variations of the present invention are readily discernible and realizable for those skilled in the art on reading the description without their having to leave the realm of the present invention.

TABLE 1

Comparison of physical-chemical parameters of two inventive high performance adsorbents based on spherical activated carbon on the one hand and commercially available microporous activated carbon in spherical form from Kureha on the other

|  | Inventive activated carbon I | Inventive activated carbon II | Commercially available activated carbon from Kureha |
| --- | --- | --- | --- |
| Total pore volume (Gurvich) ($p/p_0 = 0.995$) [$cm^3/g$]** | 0.7336 | 1.3550 | 0.5891 |
| Measure of central tendency pore diameter [Å] | 18.57 | 24.67 | 17.89 |
| BET (Multipoint, MP) ($p/p_0 = 0.05$-$0.1$) (ASTM D6556-04) [$m^2/g$]** | 1.580 | 2.197 | 1.317 |
| Carbon black method micropore volume [$cm^3/g$]* | 0.6276 | 0.9673 | 0.5240 |
| Micropore fraction of total pore volume [%]* | 85.55 | 71.39 | 88.95 |
| Adsorbed $N_2$ volume ($p/p_0 = 0.25$) weight based [$cm^3/g$]** | 423 | 650 | 349 |
| Adsorbed $N_2$ volume ($p/p_0 = 0.25$) volume based [$cm^3/cm^3$]** | 236 | 235 | 206 |
| Adsorbed $N_2$ volume ($p/p_0 = 0.995$) weight based [$cm^3/g$]** | 473 | 770 | 380 |
| Adsorbed $N_2$ volume ($p/p_0 = 0.995$) volume based [$cm^3/cm^3$]** | 264 | 279 | 224 |
| Carbon black micropore surface area [$cm^2/g$]* | 1.509 | 1.995 | 1.271 |
| Carbon black method external pore volume [$cm^3/g$] | 0.11 | 0.39 | 0.07 |
| External pore volume fraction of total pore volume [%] | 14.4 | 28.6 | 11.1 |
| Carbon black method external pore surface area [$cm^2/g$] | 71 | 202 | 46 |
| External pore surface area fraction of BET surface area (MP) [%] | 4.5 | 9.2 | 3.5 |
| Adsorbate | $N_2$ | $N_2$ | $N_2$ |
| Butane adsorption (ASTM D542-95/00) [%] | 33.5 | 59.6 | 29.2 |
| Iodine number (ASTM D4607-94/99) [mg/g] | 1.470 | 1.840 | 1.343 |
| Compressive or bursting strength (resistance to weight loading) [kg/activated carbon spherule] | 3.75 | 1.4 | 0.45 |
| Measure of central tendency diameter (ASTM D2862-97/04) [mm] | 0.52 | 0.44 | 0.44 |
| Ash content (ASTM D2866-94/04) [%] | 0.50 | 0.45 | 0.04 |
| Moisture content (ASTM D2867-04/04) [%] | 0.04 | 0.1 | 0.37 |

*micropores: pores having pore diameters ≦20 Å
**$p/p_0$ = partial pressure or partial pressure range

The invention claimed is:

1. High performance adsorbents based on activated carbon in the form of discrete grains of activated carbon, having a central tendency particle diameter, determined to ASTM D2862-97/04, in the range from 0.01 to 1.0 mm, the high performance adsorbents being characterized by the following parameters:
a Gurvich total pore volume of at least 0.7 $cm^3/g$, at least 70% of this total pore volume being formed by micropores having pore diameters of ≦20 Å,
a measure of central tendency pore diameter of not more than 30 Å,
a BET surface area of at least 1500 $m^2/g$,
an abrasion resistance of at least 95%, and
a compression or bursting strength per activated carbon grain of at least 10 newtons.

2. The high performance adsorbents based on activated carbon of claim 1, wherein the Gurvich total pore volume of the high performance adsorbents is at least 0.8 $cm^3/g$.

3. The high performance adsorbents based on activated carbon of claim 1, wherein the Gurvich total pore volume of the high performance adsorbents is in the range from 0.7 to 1.8 $cm^3/g$.

4. The high performance adsorbents based on activated carbon of claim 1, wherein at least 75% of the Gurvich total pore volume of the high performance adsorbents is formed by micropores having pore diameters of ≦20 Å.

5. The high performance adsorbents based on activated carbon of claim 1, wherein 70% to 95%, in particular 75% to 90% of the high performance adsorbents is formed by micropores having pore diameters of ≦20 Å.

6. The high performance adsorbents based on activated carbon of claim 1, wherein the carbon black method micropore volume of the high performance adsorbents which is formed by micropores having pore diameters of ≦20Å is in the range from 0.5 to 1.4 $cm^3/g$.

7. The high performance adsorbents based on activated carbon of claim 1, wherein the measure of central tendency pore diameter of the high performance adsorbents is not more than 26 Å.

8. The high performance adsorbents based on activated carbon of claim 1, wherein the BET surface area of the high performance adsorbents is in the range from 1500 $m^2/g$ to 2750 $m^2/g$.

9. The high performance adsorbents based on activated carbon of claim 1, wherein the weight-based adsorbed $N_2$ volume $V_{ads\ (wt)}$ of the high performance adsorbents, determined at a partial pressure $p/p_0$ of 0.25, is in the range from 400 to 800 $cm^3/g$ and wherein the volume-based adsorbed $N_2$ volume $V_{ads\ (vol)}$ of the high performance adsorbents, determined at a partial pressure $p/p_0$ of 0.25, is in the range from 210 to 275 $cm^3/cm^3$.

10. The high performance adsorbents based on activated carbon of claim 1, wherein the weight-based adsorbed $N_2$ volume $V_{ads\ (wt)}$ of the high performance adsorbents, determined at a partial pressure $p/po$ of 0.995, is in the range from 450 to 900 $cm^3/g$ and wherein the volume-based adsorbed $N_2$ volume $V_{ads\ (vol)}$ of the high performance adsorbents, determined at a partial pressure $p/po$ of 0.995, is in the range from 250 to 400 $cm^3/cm^3$.

11. The high performance adsorbents based on activated carbon of claim 1, wherein the carbon black method micropore surface area of the high performance adsorbents which is formed from pores having pore diameters of $\leqq 20$ Å is in the range from 1400 to 2500 m$^2$/g.

12. The high performance adsorbents based on activated carbon of claim 1, wherein the high performance adsorbents have a butane adsorption of at least 25%.

13. The high performance adsorbents based on activated carbon of claim 1, wherein the high performance adsorbents have an iodine number of at least 1350 mg/g.

14. High performance adsorbents based on activated carbon in the form of discrete grains of activated carbon, having a central tendency particle diameter, determined to ASTM D2862-97/04, in the range from 0.01 to 1.0mm, the high performance adsorbents being characterized by the following parameters:

a Gurvich total pore volume of at least 0.7 cm$^3$/g, at least 70% of this total pore volume being formed by micropores having pore diameters of $\leqq 20$ Å, a measure of central tendency pore diameter of not more than 30 Å, a BET surface area of at least 1500 m$^2$/g, an abrasion resistance of at least 95%, a compression or bursting strength per activated carbon grain of at least 10 newtons, a butane adsorption of at least 25%, and an iodine number of at least 1350 mg/g.

* * * * *